United States Patent
Lofberg

(10) Patent No.: US 7,316,659 B2
(45) Date of Patent: Jan. 8, 2008

(54) DEVICE FOR DOSAGE OF AIR

(76) Inventor: Hans Lofberg, Abylundsvagen 441, Vasterhaninge (SE) S-137 32

(*) Notice: Subject to any disclaimer, the term of this patent is extended or adjusted under 35 U.S.C. 154(b) by 353 days.

(21) Appl. No.: 10/498,658

(22) PCT Filed: Dec. 12, 2002

(86) PCT No.: PCT/SE02/02311
§ 371 (c)(1),
(2), (4) Date: Jun. 14, 2004

(87) PCT Pub. No.: WO03/055426
PCT Pub. Date: Jul. 10, 2003

(65) Prior Publication Data
US 2005/0085750 A1    Apr. 21, 2005

(30) Foreign Application Priority Data
Dec. 12, 2001    (SE)    .................... 0104187

(51) Int. Cl.
A61H 1/00    (2006.01)

(52) U.S. Cl. .......................................... 601/76; 601/77

(58) Field of Classification Search ............. 601/76–77
See application file for complete search history.

(56) References Cited

U.S. PATENT DOCUMENTS
5,024,612 A    6/1991    Van Den Honert et al.
5,823,399 A *  10/1998   Gartner ..................... 222/209

FOREIGN PATENT DOCUMENTS
EP    0 504 124    9/1992
FR    2 706 288    12/1994

* cited by examiner

Primary Examiner—Michael A. Brown
(74) Attorney, Agent, or Firm—Ostrolenk, Faber, Gerb & Soffen, LLP

(57) ABSTRACT

The invention refers to a feeder for dosing air in small quantities or pressure pulses to the external auditory meatus of a person with vertigo e.g. Ménière's disease. The feeder includes a pump body (10) with a through hole (12), one end (14) of which is connectable to an ear adapter by a flexible tube and the other end (15) of which is provided with an air pump device (16). The pump body (10) of the air pump device (16) has a manually impressionable, temporarily adjustable volume in providing a quantity of air with a pulsating overpressure of a repeatable and adjustable size.

8 Claims, 1 Drawing Sheet

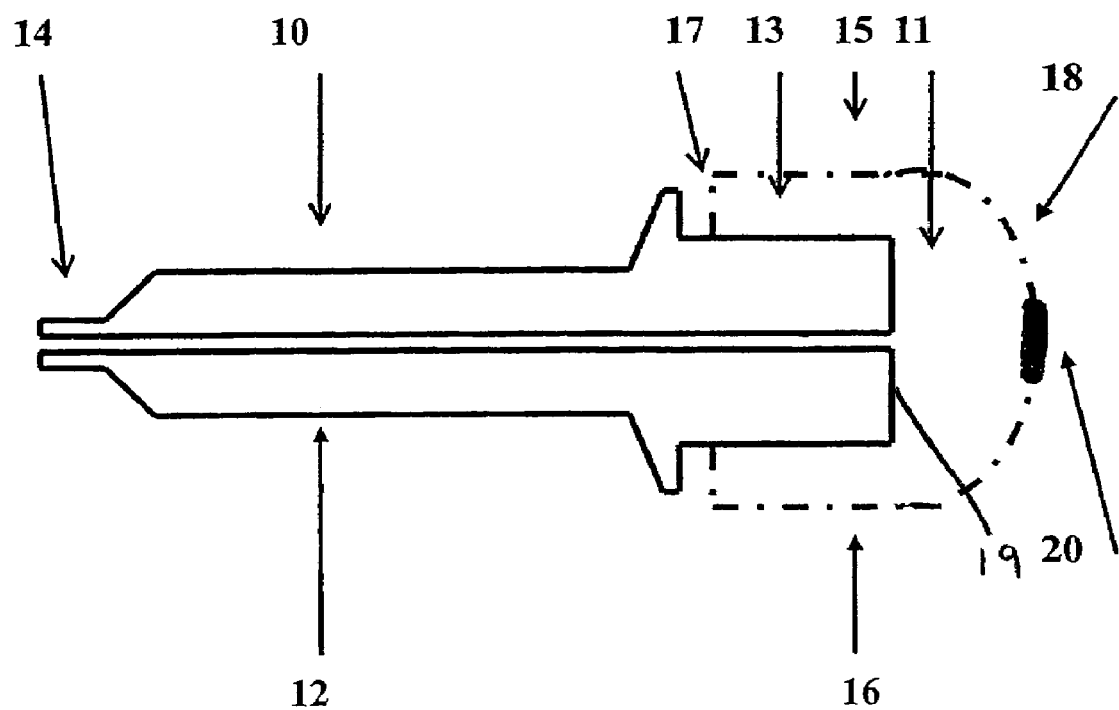

DEVICE FOR DOSAGE OF AIR

CROSS-REFERENCE TO RELATED APPLICATIONS

The present application is a 35 U.S.C. §§ 371 national phase conversion of PCT/SE02/02311, filed Dec. 12, 2002, which claims priority of Swedish Application No. 01041870, filed Dec. 12, 2001. The PCT International Application was published in the English language.

FIELD OF THE INVENTION

The present invention refers to a feeder for dosing air in small quantities or pressure pulses to the external auditory meatus of a person with vertigo e.g. Ménière's disease and including a pump body with a through hole, one end of which being connectable to an ear adapter by a flexible tube and the other end of which being provided with an air pump device.

BACKGROUND OF THE INVENTION

There are many different vertigos especially among grown-ups and one is Ménière's disease. This disease is caused by disturbances in the balance organ of the internal ear and it often leads to serious hearing impairment with deafness as a not unusual consequence. This disease and other similar vertigos are very difficult to treat. You can give medicines with tablets for expelling liquid or you can also operate, which unfortunately often leads to deafness as a consequence.

A new method to manage these diseases is to give the ducts of the internal ear a gentle "massage" with the help of a light air excess pressure and a tube installed in the tympanic membrane. This has proved effective both prophylactically and also acutely but the apparatus which up till now have been based on this method are extremely complicated and expensive. Furthermore, they are not suitable for mobile use.

SUMMARY OF THE INVENTION

The object of the present invention is to provide a simple and cheap device, which a person can carry, e.g. in his pocket, to be used anywhere when needed.

BRIEF DESCRIPTION OF THE DRAWING

The invention is more in detail described below with reference to the attached drawing, which schematically shows the invention from the side.

DETAILED DESCRIPTION OF THE PREFERRED EMBODIMENTS

The characteristic features of the invention are stated in the subsequent patent claims. Thanks to the invention a feeder according to the above has been provided, which in an excelent way fulfils its purposes at the same time as it is very cheap and easy to produce. When a person with a vertigo problem begins to feel dizzy you just pull the air dosing feeder out of your pocket or handbag. The ear adapter is put into the external auditory meatus, you adjust the position of the bellows on the pump body, and then you push your finger, e.g. your thumb, against the resilient compressible bellows a suitable number of times to create intermittent increases of pressure in the ear. To increase or decrease the air quantity you only adjust the bellows on the pump body in one or the other direction and after pumping for a while the dizziness is gone.

This air dosing feeder consists according to the invention of a pump body 10 e.g. in plastic with an assembled compressible air pump device 16. This air pump device 16 can be in the shape of a bellows 11. The pump body 10 has in this example a through hole 12. One end 14 is narrower than the other and a plastic tube is mountable with the ear adapter. The other end 15 of the pump body 10 has the shape of a neck 13, where the bellows 11 is mounted. This is possible owing to the fact that the bellows 11 has an open end 17 and therefore can be slipped on the neck 13. The bellows 11 has a bottom 18 opposite the open end 17. This bottom acts as a pressure suface. It is resilient and possible to press against the free outer end 19 of the neck 13. The position of the bellows 11 on the neck 13 can be adjusted and fixed in a suitable place along the length of the neck 13. The length of the neck 13 is matched so that by compressing the bellows 11 completely to the bottom of the outer end 19 of the neck 13 an identical amount of compressed air is guaranteed the whole time. The position of the bellows 11 on the neck 13 can be fastened by a simple hand grip. In this example the bellows can obtain the fixed position on the neck 13 only by means of friction. By adjusting the position of the bellows 11 on the neck 13 the amount of air can thus be increased or decreased with retained exactness of the pumping.

In an alternative embodiment example the bellows 11 is firmly mounted to the other end 15 of the pump body 10 at the same time as the free outer end 19 of the neck 13 is movable to and from the bottom 18 of the bellows 11 in order to obtain the repeatable constant amount of air.

To obtain the pressure of the surrounding atmosphere inside the bellows 11 after having put the ear adapter into the external auditory meatus, the bottom 18 of the bellows 11 can have an opening, e.g. in the shape of a hole 20 of about 1-3 mm. An exact pressure of the pumping is in this way guaranteed the whole time, both after the putting in the adapter into the ear and after each pumping. The hole 20 can be shut off by aid of a finger during the pumping.

The invention claimed is:

1. A feeder for dosing air to an external auditory meatus of a person, the feeder comprising:
    a pump body having a through hole and a first end at the through hole, the first end shaped to be connected to an ear adapter shaped for installation in the auditory meatus;
    a neck on the pump body at a second end of the body and at the through hole, the neck having a free outer end; and
    an air pump device comprising a resilient compressible bellows, the bellows having an open end that receives the outer end of the neck, the bellows being mounted at a selected, variable position along the neck, the bellows having a closed end opposing the outer end of the neck and operable for providing the pump body with a manually compressible and temporarily adjustable volume, the volume being adjustable as a function of the variable position of the bellows on the neck,
    wherein the feeder is operable to provide a pulsating, repeatable and adjustable quantity of air to be supplied to the auditory meatus when the closed end of the bellows is compressed toward the free outer end of the neck.

2. The feeder according to claim 1, wherein the closed end of the bellows is provided with an opening, which can be closed by aid of a finger during use of the feeder.

3. The feeder according to claim 1, wherein the neck has a substantially constant diameter.

4. The feeder according to claim 1, wherein the feeder is suitable for treating a person with vertigo.

5. The feeder according to claim 1, wherein the bellows is compressible against the free outer end of the neck.

6. The feeder according to claim 1, wherein the air pump device is held on the neck by a grip.

7. The feeder according to claim 1, wherein the air pump device is held on the neck by friction.

8. The feeder according to claim 1, wherein the air pump device is mounted on the neck by the open end of the bellows on the neck.

* * * * *